US005541330A

United States Patent [19]

Wear et al.

[11] Patent Number: 5,541,330
[45] Date of Patent: Jul. 30, 1996

[54] ION-SENSITIVE COMPOUNDS

[75] Inventors: Trevor J. Wear, South Harrow; Christopher P. Moore, Harrow; Paul D. Beer, North Oxford; John W. Wheeler, Perton, all of United Kingdom

[73] Assignee: Eastman Kodak Company, Rochester, N.Y.

[21] Appl. No.: 440,269

[22] Filed: May 12, 1995

Related U.S. Application Data

[63] Continuation-in-part of Ser. No. 104,136, Aug. 10, 1993, abandoned.

[30] Foreign Application Priority Data

Dec. 10, 1991 [GB] United Kingdom ............... 9126146

[51] Int. Cl.[6] .................... C07D 213/22; C07D 213/38
[52] U.S. Cl. .................... 546/257; 546/258; 544/344
[58] Field of Search .................... 546/257, 258

[56] References Cited

U.S. PATENT DOCUMENTS 4,151,165  4/1979  Shiga et al. ...................... 546/257
4,859,777  8/1989  Toner ...................... 546/256
4,981,961  1/1991  Ngo ...................... 536/112

OTHER PUBLICATIONS

Chemical Abstracts, vol. 108, No. 3, 18 Jan. 1988, Columbus, Ohio, US, Abstract No. 21736h, P. G. Potvin et al, "Design of Cationic and Anionic Receptors, Catalysts, and Carriers", p. 586.

P. D. Beer et al, "Anion Recognition by New Acyclic Quaternary Polybipyridinium Receptors", Journal Of The Chemical Society, Chemical Communications, No. 17, 1 Sep. 1992, Letchworth, GB, pp. 1225–1227.

*Primary Examiner*—Robert W. Ramsuer
*Assistant Examiner*—John Peabody
*Attorney, Agent, or Firm*—John R. Everett

[57] ABSTRACT

Ion-sensitive compounds are provided comprising a quaternary polypyridinium receptor designed to bind anionic species by the formation of a receptor-substrate complex. The receptor comprises one or more quaternary 2,2'-bipyridyl moieties. The compounds are of use in applications requiring anion detection or removal.

8 Claims, No Drawings

ION-SENSITIVE COMPOUNDS

CROSS-REFERENCE TO RELATED APPLICATIONS

This is a continuation-in-part of application Ser. No. 08/104,136, filed Aug. 10, 1993, now abandoned.

The invention relates to ion-sensitive compounds. More particularly, the invention relates to ion-sensitive compounds comprising a quaternary polypyridinium receptor designed to bind anionic species by the formation of a receptor-substrate complex. The compounds can be used to detect anions in solution by sensing the electrochemical change which results from the formation of the complex.

Anion receptors comprising a plurality of quaternary amine groups are known. Examples of such compounds may be seen in P. G. Potvin and J-M Lehn, *Prog. Macrocyclic Chem.*, 1987, 3, 214.

L. A. Summers, "The Bipyridinium Herbicides", Academic Press, New York, 1980, describes the use of certain compounds comprising diquaternary 2,2'-bipyridinium moieties in herbicidal applications.

There is a continuing need to provide new receptor compounds for a variety of applications. For example, such compounds may be incorporated in electrochemical sensors for anion determination. A number of electrochemical sensors utilizing ion receptors are known. Alternatively, such compounds may be used in removal devices where levels of a given anion need to be kept low. A number of removal devices utilizing ion receptors are known. It is also desirable to provide receptor compounds which can be readily synthesized.

The invention provides a new class of anion receptors derived from diquaternary bipyridinium groups joined together via flexible linking groups. The molecules are constructed so as to be able to fold around the particular anions, especially spherical anions such as halide ions e.g. chloride and bromide, in order to maximize electrostatic interactions between the multiplicity of electron deficient centers and the electron rich surface of the anion in a cooperative fashion. Thus, the compounds of the invention are capable of capturing and electrochemically recognizing anions. The compounds can show selectivity for a particular anion in a mixture of anions.

The ion-sensitive compounds of the invention have the formula $A^{n+}B^{n-}$ wherein A represents a cation capable of forming a receptor-substrate complex with an anion, B represents one or more suitable counter anions and n is an integer from 3 to 10, characterized in that the cation is an anion receptor represented by the formula $R^1$—Y—$R^2$ wherein Y is represented by the structure

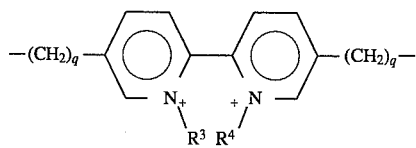

each q independently is an integer from 1 to 6;

$R^3$ and $R^4$ are each independently H or a lower alkyl group having from 1 to 4 carbon atoms, or $R^3$ and $R^4$ taken together represent an ethylene bridging group;

$R^1$ and $R^2$ are each independently selected from organic cations and non-ionic organic groups wherein at least one of $R^1$ and $R^2$ is an organic cation and the combined ionic charge of $R^1$ and $R^2$ is from 1 to 8; or, $R^1$ is H and $R^2$ is —X—Y—H wherein X is a linking group and Y is as defined above; or, $R^1$ and $R^2$ taken together represent —X—Y—X— wherein X and Y are as defined above.

The invention also provides a method of sensing an anion in solution by contacting the anion with a receptor for the anion to form a receptor-substrate complex and sensing a detectable change which results from the formation of the complex characterized in that the receptor is a compound of the invention.

Preferred compounds having the formula defined above include compounds wherein q is 1. $R^3$ and $R^4$ may each be methyl.

Examples of non-ionic groups from which $R^1$ and $R^2$ may be chosen include alkylamino, poly(alkylamino), arylamino, poly(arylamino), alkylamido, arylamido, alkylphosphoramido, arylphosphoramido, alkylsulphonamido, arylsulphonamido, alkyloxycarbonyl, aryloxycarbonyl, pyridyl and bipyridyl.

Examples of organic cations from which $R^1$ and $R^2$ may be chosen include the quaternized forms of the non-ionic groups listed above. Particular examples are 2,2'-bipyridinium, 4,4'-bipyridinium and —[$^+N(R^5)_2$—$R^6$]$_p$—$R^7$ wherein each $R^5$ independently is hydrogen or an alkyl group of from 1 to 4 carbon atoms; $R^6$ is an alkylene group of from 1 to 3 carbon atoms; $R^7$ is hydrogen or —$N(R^5)_3$ and p is an integer from 1 to 4.

Preferred compounds include those wherein both $R^1$ and $R^2$ are organic cations.

Examples of suitable linking groups represented by X include alkylene, arylene, and quaternized or unquaternized amine- or polyamine-containing groups such as alkylamino, arylamino, aminoalkyleneamino, amino[poly(alkyleneamino)], bipyridyl and bipyridylamino. Preferred groups include 4,4'-bipyridinium and —[$^+N(R^5)_2$—$R^6$]$_p$—$N^+$($R^5)_2$— wherein $R^5$, $R^6$ and p are as defined above.

B represents any suitable counter anion which together with the polypyridinium moiety is capable of forming a stable compound. A suitable counter anion does not interfere with the function of the cationic receptor e.g. by covalent bond formation or otherwise, and anions forming a complex with the receptor are excluded from being counter anions. Examples of such counter anions include sulphate, nitrate, phosphate, borate and halide e.g. iodide. Preferably, B represents a weakly coordinating anion such as hexafluorophosphate and tetrafluoroborate.

In the definitions given above, all alkyl, alkylene, aryl and arylene groups, when present as such or as part of another substituent, are optionally substituted.

Specific examples of preferred compounds of the invention are as follows.

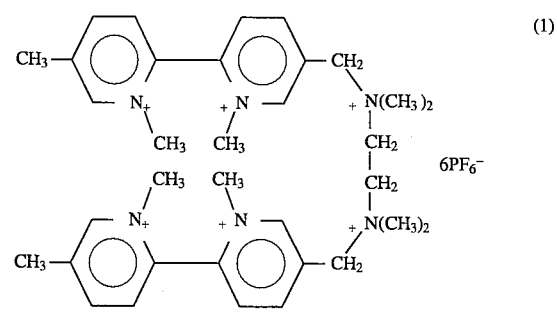

(1)

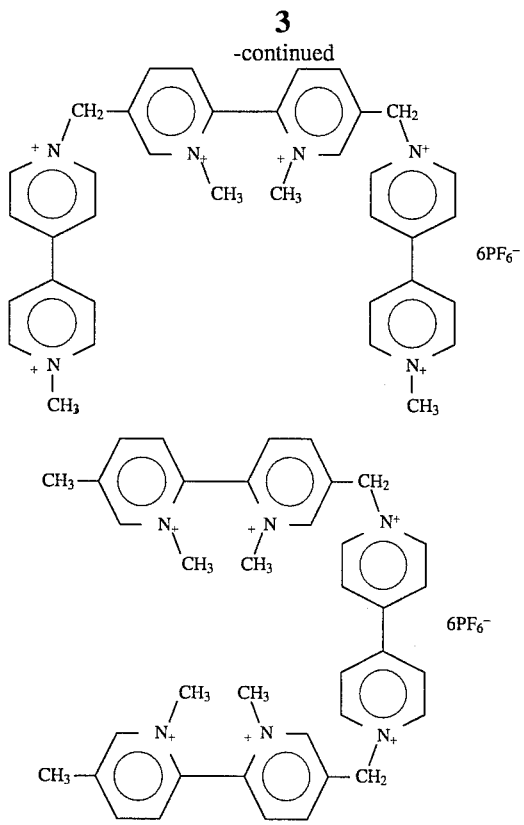

The compounds of the invention can be prepared using 5,5'-dibromoalkyl-2,2'-bipyridyl or 5-bromoalkyl-5'-alkyl-2,2'-bipyridyl as the starting materials. Reaction of the dibromo substituted material with an appropriate amine e.g. 4,4'-bipyridyl followed by quaternization with an alkylating agent e.g. methyl iodide will produce the 5,5'-disubstituted compounds of the invention in which the 2,2'-bipyridinium moiety is flanked by positively charged groups. Alternatively, the dibromo compound can be reacted with a variety of compounds which have been deprotonated to give a mono-anion e.g. the mono anion produced by deprotonating 2,2'-bipyridyl with butyl lithium.

Reaction of the monobromo substituted material with an appropriate diamine e.g. N,N'-dimethyl ethylenediamine followed by quaternization with an alkylating agent will produce compounds of the invention in which two 2,2'-bipyridinium moieties are attached through a linking group. Other bifunctional linking groups may be reacted with the monobromo substituted material in this way with or without formation of a di-anion by deprotonation.

The compounds of the invention are intended for use in commercial applications such s electrochemical sensors. Chapter 10 of the textbook *Inclusion Compounds*, Vol. 5, Edited by J. L. Atwood, J. E. D. Davies and D. D. MacNicol, 1991 Oxford University Press describes such chemical sensors.

A particular example of such use is the ion-selective electrode (ISE). The preparation and use of ion-selective electrodes is well documented in the patent literature and elsewhere e.g. European Patents Nos. 0 082 518 and 0 174 572, and *Anal, Chem.,* 1989, 61, 499-503 "Anion-Selective Electrodes based on a Hydrophobic Vitamin B12 Derivative" and "Ion-selective Electrodes in *Analytical Chemistry*" Edited by H. Freiset, Plenum Press, 1978, A commonly used type of ion-selective electrode is a polyvinylchloride (PVC) matrix membrane electrode. The membrane is generally prepared by incorporating liquid ion exchanger components (ion-sensitive compound and mediator/plasticizer) in PVC with the aid of a solvent such as tetrahydrofuran or cyclohexanone, and the solvent is allowed to evaporate, leaving a flexible membrane with liquid ion exchanger components trapped in a PVC matrix. PVC matrix membrane electrodes may be designed on the principles of conventional glass electrodes or of coated rods or wires. A coated wire electrode may be readily made by dipping a platinum wire in a solution of PVC/sensor/mediator components in tetrahydrofuran or cyclohexanone.

In use, the electrode is contacted with a solution containing the ions to be sensed. The membrane potential generated can be related to the activity of the ions sensed by the electrode.

Specific examples of the preparation of compounds of the invention are given as follows.

EXAMPLE 1

N,N'-Bis(5'-methyl-2,2'-bipyridyl-5-methylene)-N,N'-dimethyl-ethylene-diamine

N,N '-Dimethyl ethylene diamine (76 mg. 0.86 mmol) was dissolved in acetonitrile (30 cm$^3$), potassium carbonate (2.64 g, 19.1 mmol) added and the mixture heated to reflux under nitrogen. To this was added dropwise a solution of 5-bromomethyl-5'-methyl-2,2'-bipyridyl (0.50 g, 1.90 mmol) in acetonitrile (30 cm$^3$) with stirring and the resultant mixture heated at reflux for 3 h. After this time the mixture was cooled to room temperature, the solid removed by filtration and the solvent removed from the filtrate under reduced pressure to give a deep orange residue. This was then chromatographed on alumina using dichloromethane/methanol (99.1) as elutant. A pale orange band was collected. After removal of the solvent the product was recrystallized from acetonitrile to give small off-white crystals of the required ligand (0.17 g, 43%) m.p. 160°–161° C. M.S.(FAB) [m/z+H]$^+$453,[CH$_2$bipyCH$_2$N(Me)CH$_2$]$^+$226, [CH$_2$bipyCH$_2$]$^+$183. I.R. 3000 cm$^{-1}$ (aromatic CH stretch), 2850/2800 cm$^{-1}$ (aliphatic CH stretch), 1600/1580 cm$^{-1}$ (C=C/C=N ring stretch) $^1$H NMR (CDCl$^3$, 270 MHz) δ: 2.24 (6H, s, bipyCH$_2$NC$\underline{H}_3$), 2.39 (6H, s, bipyC$\underline{H}_3$), 2.59 (4H, s, bipyCH$_2$NC$\underline{H}_2$), 3.58 (4H, s, bipyC$\underline{H}_2$), 7.61 (2H, d, $^3$J=8.1 Hz, bipyH$_{4'}$), 7.77 (2H, d, $^3$J=8.2 Hz, bipyH$_4$), 8.26 (2H, d, $^3$J=8.2 Hz, bipyH$_3$), 8.30 (2H, d, $^3$J=8.1 Hz,bipyH$_{3'}$), 8.49 (2H, s, bipyH$_{6'}$), 8.56 (2H, s, bipyH$_6$) $^{13}$C NMR (CDCl$_3$, 67.8 MHz) δ: 18.35 (bipyC$\underline{H}_3$). 42.55 (bipyCH$_2$NC$\underline{H}_3$), 55.11 and 59.76 (bipyC$\underline{H}_2$NC$\underline{H}_2$), 120.41, 120.50, 133.22, 134.12, 137.43, 137.57, 149.59, 149.70, 153.59 and 155.25 (aromatic C) Analysis calculated for C$_{28}$H$_{32}$N$_6$; C: 74.3%, H: 7.1%, N: 18.6%. Found C: 74.5%, H: 6.8%, N: 18.9%.

N,N'-Bis(N,N',5'-trimethyl-2,2'-bipyridyl-5-methylene)N,N,N'N'-tetramethyl-ethylene-diammonium hexa(hexafluorophosphate) (1)

The ligand (70 mg, 0.16 mmol) was dissolved in dimethyl sulphate (10 cm$^3$) with stirring and heated to 75° C. under nitrogen for 7 days. The solution was cooled to room temperature and the precipitate collected for filtration. The so lid was washed with acetone (3×10 cm$^3$) and then dissolved in water (15 cm$^3$). To this solution was added a saturated aqueous solution of ammonium hexafluorophosphate until precipitation ceased to occur. The precipitate was collected by filtration, washed with water (2×10 cm$^3$) and dried under vacuum over silica gel to give a white solid (73 mg). The solid was dissolved in acetonitrile under nitrogen with stirring. To this was added methyl iodide and the resultant solution heated at reflux for 18 days. After this time the mixture was cooled to room temperature. A solution of tetra-butyl ammonium chloride (0.2g in 5 cm³ of acetonitrile) was added to precipitate the product as the chloride salt. This was collected by filtration, dried, then dissolved in water (10 cm³). To the solution was added a saturated aqueous solution of ammonium hexafluorophosphate until precipitation ceased to occur. The solid was collected by filtration, washed with water (2×5 cm³) and dried under vacuum over silica to give the hexa-cationic receptor (1) having six hexafluorophoshphate (PF6±) counter anions (24 mg, 11%) m.p. 195° C. (decomp). M.S. (FAB) [m/z-PF$_6$—]$^+$ 1267, [m/z-2PF$_6$—]$^+$1122, [m/z-CH$_3^+$-2PF$_6$—]$^+$1107, [m/z-CH$_3^+$-3PF$_6$—]$^+$962, [m/z-4CH$_3^+$-5PF$_6$—]$^+$629 $^1$H NMR (DMSO, 400 MHz) δ: 2.68 (6H, s, bipy$\underline{CH}_3$), 3.21 and 3.24 (12H, 2s, bipyCH$_2$N$^{+(\underline{CH}}_3)_2$, 4.14 and 4.24 (12H, 2s, bipyN$^+$-$\underline{CH}_3$), 4.27 (4H, s, bipyCH$_2$N$^+\underline{CH}_2$) 5.02 (4H, s, bipy $\underline{CH}_2$), 8.19 (2H, d, $^3$J=8.1 Hz, bipyH$_4$'), 8.63 (2H, d, $^3$J=8.1 Hz, bipyH$_4$), 8.79 (2H, d, $^3$J=8.1 Hz), bipyH$_3$'), 9.07 (2H, d, $^3$J=8.1 Hz, bipyH$_3$), 9.42 (2H, s, bipyH$_6$ '), 9.53 (2H, s, bipyH$_6$) $^{13}$C NMR (DMSO, δ: 18.12 (bipy$\underline{CH}_3$), 47.42 and 48.11 (bipyN$^{+-\underline{CH}}_3$), 49.58 and 49.74 (bipyCH$_2$N$^{+(\underline{CH}}_3)_2$), 57.98 (bipyCH$_2$N$^+\underline{CH}_2$), 62.60 (bipyCH$_2$), 129.47, 129.70, 131.22, 139.78, 141.63, 144.67, 146.72, 149.14, 151.00 and 152.09 (aromatic C). Analysis calculated for C$_{34}$H$_{50}$F$_{36}$N$_6$P$_6$; C: 28.9%, H: 3.6%, N: 6.0%. Found C: 29.4%, H: 3.6%, N: 6.1%

Anion Binding

The extent of the ion sensitivity i.e. anion capturing properties of the compound was investigated using $^1$H NMR. The capture of an anion by the receptor influences the chemical environment of the receptor by causing conformational changes. This in turn gives rise to changes in the observed chemical shifts of protons adjacent to the binding site.

The receptor (1) displayed substantial shifts of the signals of the $^1$H NMR spectrum following the addition of one equivalent of tetrabutyl ammonium chloride to a solution of the receptor (1) in d6-dimethyl sulphoxide solution. More particularly, there were substantial changes in chemical shift of those protons associated with the anion binding site. Analysis of the signals confirmed the formation of a complex between the receptor and the chloride ion.

Under identical experimental conditions no significant changes in chemical shift were observed with isolated dication species such as N,N',5,5'-tetramethyl- 2-2'-bipyridinium hexafluorophosphate. These results confirmed the formation of a complex between the receptor and the chloride anion rather than being as a result of simple anion exchange.

In conclusion, the experiment shows that compound (1) is sensitive to chloride i.e. can detect the presence of chloride.

EXAMPLE 2

5,5'-Bis(4,4'-bipyridyl-N-methylene)-2,2'-bipyridyl bis(hexafluorophosphate)

4,4'-Bipyridyl (18.2 g, 116.5 mmol) was dissolved in acetonitrile (700 cm³) with stirring under nitrogen and heated to reflux. A solution of 5, 5'-bis(bromomethyl)-2,2-bipyridyl (0.80 g, 2.34 mmol) in acetonitrile (300 cm³) was added dropwise and the resultant solution heated at reflux for 48 h. The mixture was then cooled to room temperature and the volume of the solvent reduced to 400 cm³. The solid was collected by filtration, washed with acetonitrile (3×50 cm³) and dried under vacuum. The solid was then dissolved in water (250 cm³) with stirring and a saturated aqueous solution of ammonium hexafluorophophate added until no further precipitation occurred. The mixture was stirred for 1 h to ensure complete precipitation of the product. This was then collected by filtration, washed with water (3×20 cm³) and dried under vacuum over silica gel to produce a white solid (1.61 g, 88%), m.p.>300° C. M.S.(FAB) [m/z-PF$_6$—]$^+$639.5, [m/z-2PF$_6$—]$^+$493.5, [m/z-4,4'-bipyridyl-2PF$_6$—]$^+$338.4, I.R. 3140/3060/3040 cm$^{-1}$ (aromatic CH stretch), 1645/1605/1555 cm$^{-1}$ (C=C/C=N ring stretch), 840 cm (br, PF$_6$—) $^1$H NMR (DMSO, 270 MHz) δ: 6.01 (4H, s, bipy$\underline{CH}_2$), 8.04 (4H, d, $^3$J=5.9 Hz, 4,4'H$_3$,'), 8.16 (2H, d, $^3$J=8.4 Hz, bipyH$_4$), 8.46 (2H, d, $^3$J=8.4 Hz, bipyH$_3$), 8.68 (4H, d, $^3$J=6.7 Hz, 4,4'H$_3$), 8.89 (4H, d, $^3$J=5.9 Hz, 4,4'H$_2$'), 8.97 (2H, s, bipyH$_6$), 9.42 (4H, d, $^3$J=6.7 Hz, 4,4'H$_2$) $^{13}$C NMR (DMSO, 67.8 MHz) δ: 60.25 (bipy$\underline{CH}$), 120.79, 121.91, 125.88, 130.67, 137.93, 140.80, 145.46, 149.78, 150.86, 152.91 and 155.19 (aromatic C) Analysis calculated for C$_{32}$N$_{26}$F$_{12}$N$_6$P$_2$;C: 49.0%, H: 3.3%, N: 10.7%. Found C: 48.7%, H: 3.3%, N: 10.4%.

5,5'-Bis(N'-methyl-4,4'-bipyridinium-N-methylene)-2,2,'-bipyridyl tetra(hexafluorophosphate)

The white solid (0.30 g. 0.38 mmol) was dissolved in nitromethane (10 cm³) with stirring. To this was added methyl iodide (10 cm³) and the resultant solution heated to reflux for 24 h. After cooling to room temperature the orange precipitate was collected by filtration and dried under vacuum. The solid was then dissolved in water (200 cm³) with warming and a saturated aqueous solution of ammonium hexafluorophosphate added until no further precipitation occurred. The solid was collected by filtration, washed with water (2×20 cm³) and dried under vacuum over silica gel to give the tetra-cationic receptor as a white solid (0.38 g. 89%), m.p.>300° C. M.S. (FAB) [m/z-PF$_6$—]$^+$959(w), [m/z-2PF$_6$—]$^+$814, [m/z-3PF$_6$—]$^+$669. I.R. 3120/3100 cm$^{-1}$ (aromatic CH stretch), 1640/1600/1580 cm$^{-1}$ (C=C/C=N ring stretch), 840 cm$^{-1}$ (br, PF$_6$—) $^1$H NMR (CD$_3$CN, 270 MHz) δ: 4.40 (6H, s, 4,4 'N$^+$-$\underline{CH}_3$), 5.93 (4H, s, bipy $\underline{CH}_2$), 8.04 (2H, d, $^3$J=8.2 Hz, bipyH$_4$) 8.36 (4H, d$^3$J=6.6 Hz, 4,4'H$_3$'), 8.42 (4H, d, $^3$J=6.8 Hz, 4,4'H$_3$), 8.54 (2H, d, $^3$J=8.1 Hz, bipyH$_3$), 8.83 (2H, s, bipyH$_6$), 8.84 (4H, d, $^3$J=6.6 Hz, 4.4 'H$_2$ '), 9.02 (4H, d, $^3$J=7.0 Hz, 4,4'H$_2$) $^{13}$C NMR (DMSO, 22.5 MHz) δ: 48.02 (4,4'N+-$\underline{CH}_3$), 60.80 (bipy$\underline{CH}_2$), 120.88, 126.12, 127.06, 130.48, 138.08, 145.95, 146.57, 148.16, 149.33, 149.82 and 155.22 (aromatic C) Analysis calculated for C$_{34}$H$_{32}$F$_{24}$N$_6$P$_4$; C: 37.0%, H: 2.9%, N: 7.6%. Found C: 36.4%, H: 2.7%, N: 77.7%.

N,N '-Dimethyl-5,5'-bis(N'-dimethyl-4,4'-bipyridinium-N-methylene)- 2,2'bipyridyl hexa(hexafluorophosphate) (2)

The tetra-cationic receptor (100 mg, 0.091 mmol) was dissolved in acetonitrile (5 cm3). To this was added dimethyl sulphate (5 cm³) and the resultant solution heated at 80° C. under nitrogen with stirring for 48 h. After this time the solution was cooled to room temperature and dichloromethane (20 cm³) added to precipitate the product as a yellow solid. This was collected by filtration and washed with dichloromethane (2×10 cm3). The solid was then dissolved in water (50 cm³) and a saturated aqueous solution of ammonium hexafluorophosphate added until precipitation ceased to occur. The product was collected by filtration, washed with water (2×10 cm³) and dried under vacuum over silica gel to give as a white solid (2) the hexacationic receptor (2) having six hexafluorophosphate (PF6±) counter anions (92 mg, 71%), m.p.>300° C. M.S. (FAB) [m/z-2PF$_6$—)$^+$ 1134, [m/z-3PF$_6$—]$^+$989, [4,4'-CH$_3$]$^+$171 I.R. 3150/3110 cm$^{-1}$ (aromatic CH stretch). 1645/1605/1590 cm$^{-1}$ (aliphatic CH stretch), 840 cm$^{-1}$ (br, PF$_6$—) $^1$H NMR (DMSO, 400 MHz) δ: 4.13 (6H, s, 4,4'N$^+$-$\underline{CH}_3$), 4.45 (6H, s, bipyN$^+$-$\underline{CH}_3$), 6.30 (4H, s, bipyCH$_2$), 8.47 (2H, d, $^3$J=8.1 Hz, bipyH$_4$), 8.75 (4H, d, $^3$J=5.7 Hz, 4,4'H$_3$,'), 8.91 (4H, d, $^3J$=5.7 Hz, 4,4'$H_3$), 9.07 (2H, d, $^3J$=7.9 Hz, bipy$H_3$), 9.31 (4H, d, J=5.8 Hz, 4,4'$H_2$'), 9.49 (4H, d, J=5.8 Hz, 4,4'$H_2$), 9.67 (2H, s, bipy$H_6$) $^{13}C$ NMR (DMSO, 100.6 MHz) δ: 47.94 and 48.20 (bipyN$^+$-$CH_3$ and 4,4'N$^+$-$CH_3$), 59.21 (bipy $CH_2$), 126.17, 126.99, 130.75, 135.97, 142.87, 146.71, 146.88, 147.41, 147.77, 149.87 and 150.15 (aromatic C). Analysis calculated for $C_{36}H_{38}F_{36}N_6P_6$; C: 30.4%, H: 2.7%, N: 5.9%. Found C: 24.8%, H: 2.5%, N: 5.9%.

Artion Binding

The receptor (2) displayed substantial shifts of the signals of the $^1H$ NMR spectrum following the addition of one equivalent of tetrabutyl ammonium chloride to a solution of the receptor (2) in d6-dimethyl sulphoxide solution. More particularly, there were substantial changes in chemical shift of those protons associated with the anion binding site. Analysis of the signals confirmed the formation of a complex between the receptor and the chloride ion.

Under identical experimental conditions no significant changes in chemical shift were observed with isolated dication species such as N,N'5,5'-tetramethyl- 2,2'bipyridinium hexafluorophosphate and N,N'-dimethyl-4,4'-bipyridinium hexafluorophosphate. These results confirmed the formation of a complex between the receptor and the chloride anion rather than being as a result of simple anion exchange.

In conclusion, the experiment shows that compound (2) is sensitive to chloride i.e. can detect the presence of chloride.

EXAMPLE 3

N,N '-Bis(5'-methyl-2,2'-bipyridyl-5-methylene)-4,4'-bipyridinium bis(hexafluorophosphate)

5-Bromomethyl-5'-methyl-2,2'bipyridyl (300 mg, 1.14 mmol) and 4,4'-bipyridyl (84 mg, 0.54 mmol) were dissolved in acetonitrile (20 cm3) with stirring. The solution was then heated to reflux for 24 h. After cooling to room temperature the precipitate was collected by filtration, washed with dichloromethane (2×10 cm3) and dried under vacuum. It was then dissolved in water (75 cm$^3$) and a saturated aqueous solution of ammonium hexafluorophosphate added until precipitation ceased to occur. The solid was collected by filtration, washed with water (2×10 cm$^3$) and dried under vacuum over silica gel to give a white powder. (343 mg, 78%), m.p.>275° C. (decomp). M.S.(FAB) [m/z+H]$^+$813, [m/z-PF$_6^-$]$^+$667, [m/z-2PF$_6^-$]$^+$ 522. I.R. 3120/3090 cm$^{-1}$ (aromatic CH stretch), 2920 cm$^{-1}$ (aliphatic CH stretch), 1640/1600/1585 cm$^{-1}$ (C=C/C=N ring stretch), 840 cm$^{-1+}$ (br, PF$_6^-$) $^1H$ NMR (CD$_3$ CN, 270 MHz) δ: 2.39 (6H, s, bipy$CH_3$), 5.90 (4H, s, bipy$CH_2$), 7.73 (2H, d, $^3J$=8.1 Hz, d, $^4J$=1.5 Hz, bipy$H_4$,), 7.98 (2H, d, $^3J$=8.3 Hz, d, $^4J$=2.2 Hz, bipy$H_4$), 8.33 (2H, d, $^3J$=8.33 Hz, bipy$H_3$,), 8.39 (4H, d, $^3J$=7.0 Hz, 4,4'$H_3$), 8.48 (2H, d, $^3J$=8.2 Hz, bipy$H_3$), 8.52 (2H, m, bipy$H_6$'), 8.78 (2H, d, $^3J$=1.8 Hz, bipy$H_6$), 9.02 (4H, d, $^3J$=7.0 Hz, 4.4'$H_2$) $^{13}C$ NMR (DMSO, 22.5 MHz) δ: 18.22 (bipy$CH_3$), 61.43 (bipy$CH_2$), 120.70, 127.66, 130.06, 134.68, 138.19, 138.32, 146.32, 149.80, 150.09, 152.34 and 156.69 (aromatic C). Analysis calculated for $C_{34}H_{30}F_{12}N_6P_2$; C: 50.3%, H: 3.7%, N: 10.3%. Found C: 50.1%, H: 3.4%, N: 10.2%.

10 N,N '-Bis(N,N', 5'-trimethyl-2,2'-bipyridinium-5-methylene)-4,4-bipyridinium bis(hexafluorophosphate) (3)

The white powder (200 mg. 0.25 mmol) was dissolved in acetonitrile (20 cm$^3$) under nitrogen. To this was added methyl iodide (10 cm$^3$) and the resultant solution heated at reflux for 6 days. After cooling to room temperature the solvent was removed under reduced pressure and the red solid dissolved in water (50 cm$^3$). To this was added a saturated aqueous solution of ammonium hexafluorophosphate until precipitation ceased to occur. The precipitate was collected by filtration, washed with water (2×10 cm$^3$) and dried under vacuum over silica gel. The solid was then dissolved in acetonitrile (15 cm$^3$), methyl iodide (10 cm$^3$) added and the solution heated at reflux under nitrogen for 10 days. After cooling to room temperature the methyl iodide was removed under reduced pressure. Then a saturated solution of tetrabutyl ammonium chloride in acetonitrile was added dropwise until no further precipitation occurred. The solid was collected by filtration and washed with acetonitrile (2×10 cm$^3$). It was then dissolved in water (15 cm$^3$), a saturated aqueous solution of ammonium hexafluorophosphate added until no further precipitation occurred. The solid was collected by filtration, washed with water (2×10 cm$^3$) and then dried under vacuum over silica gel. The resultant solid was dissolved in acetonitrile (10 cm$^3$), dimethyl sulphate (5 cm$^3$) added and the solution stirred at 75° C. under nitrogen for 48 h. After cooling to room temperature the precipitate was collected by filtration. It was then washed with acetonitrile (3×20 cm$^3$). The solid was dissolved in water (20 cm$^3$) and a saturated aqueous solution of ammonium hexafluorophosphate added until no further precipitation occurred. The white solid was then collected by filtration, washed with water (3×10 cm$^3$) and dried under vacuum over silica gel to give as a white powder (3) the hexacationic receptor (3) having six hexafluorophosphate (PF6±) counter anions (158 mg, 44%). M.S. (FAB) [m/z-2PF$_6^-$]$^+$ 1161 $^1H$ NMR (DMSO, 400 MHz ) δ: 2.64 (6H, s, bipy $CH_3$), 4.05/4.16 (12H, 2s, bipyN$^+$-$CH_3$), 6.29 (4H, s, bipy $CH_2$), 8.25 (2H, d, $^3J$=8.1 Hz, bipy$H_4$'), 8.52 (2H, d, $^3J$=8.2 Hz, bipy$H_4$), 8.74 (2H, d, $^3J$=8.1 Hz, bipy$H^{3}$'), 8.89 (4H, d, $^3J$=6.4 Hz, 4,4'$H_3$), 9.06 (2H, d, $^3J$=8.1 Hz, bipy$H_3$), 9.36 (2H, s, bipy$H_6$'), 9.52 (4H, d, $^3J$=6.3 Hz, 4,4'$H_2$), 9.67 (2H, s, bipy$H_6$) $^{13}C$ NMR (DMSO, 100.6 MHz) δ: 18.18 (bipy $CH_3$), 47.38 and 47.98 (bipyN$^+$-$CH_3$), 59.42 (bipy$CH_2$). 127.15, 129.80, 131.03, 135.03, 135.62, 139.94, 141.69, 143.75, 146.72, 146.91, 147.40, 149.11, 149.54 and 150.25 (aromatic C). Analysis calculated for $C_{38}H_{42}F_{36}N_6P_6$·2$H_2O$; C: 30.7%, H: 3.1%, N: 5.6%. Found C: 30.5%, H: 2.9%, N: 5.6%.

Artion Binding

The receptor (3) displayed substantial shifts of the signals of the $^1H$ NMR spectrum following the addition of one equivalent of tetrabutyl ammonium chloride and tetrabutyl ammonium bromide, respectively, to a solution of the receptor (2) in d6-dimethyl sulphoxide solution. More particularly, there were substantial changes in chemical shift of those protons associated with the anion binding site. Analysis of the signals confirmed the formation of complexes between the receptor and the chloride ion and the bromide ion, respectively.

Under identical experimental conditions no significant changes in chemical shift were observed with isolated dication species such as N,N',5,5'-tetramethyl- 2,2'-bipyridinium hexafluorophosphate and N,N'-dimethyl-4,4'-bipyridinium hexafluorophosphate. These results confirmed the formation of a complex between the receptor and the chloride or bromide anion rather than being as a result of simple anion exchange.

In conclusion, the experiment shows that compound (3) is sensitive to chloride and bromide i.e. can detect the presence of chloride and bromide.

We claim:

1. An ion-sensitive compound having the formula $A^{n+}B^{n-}$ wherein A represents a cation capable of forming a receptor-substrate complex with an anion, B represents one or more counter anions and n is an integer from 3 to 10, wherein the cation is an anion receptor represented by the formula $R^1-Y-R^2$ wherein Y is represented by the structure

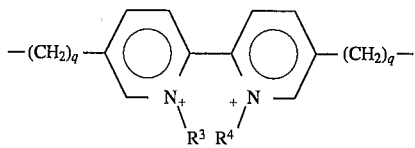

each q independently is an integer from 1 to 6;

$R^3$ and $R^4$ are each independently H or a lower alkyl group having from 1 to 4 carbon atoms, or $R^3$ and $R^4$ taken together represent an ethylene bridging group;

$R^1$ and $R^2$ are each independently selected from organic cations and non-ionic organic groups, wherein:
  (a) the non-ionic group is selected from the group consisting of alkylamino, poly(alkylamino), arylamino, poly(arylamino), alkylamido, arylamido, alkylphosphoramido, arylphosphoramido, alkylsulphonamido, arylsulphonamido, alkyloxycarbonyl, aryloxycarbonyl, pyridyl and bipyridyl;
  (b) the organic cation is selected from the group consisting of the quaternized forms of the non-ionic groups of 2,2'-bipyridinium, 4,4'-bipyridinium and $-[^+N(R^5)_2-R^6]_p-R^7$ wherein each $R^5$ independently is hydrogen or an alkyl group of from 1 to 4 carbon atoms; $R^6$ is an alkylene group of from 1 to 3 carbon atoms; $R^7$ is hydrogen or $-N(R^5)_3$ and p is an integer from 1 to 4; and
  (c) at least one of $R^1$ and $R^2$ is an organic cation according to b); or $R^1$ is H and $R^2$ is $-X-Y-H$ wherein X is selected from the group consisting of alkylene, arylene, and quaternized or unquaternized amine- or polyamine-containing groups selected from the group consisting of alkylamino, arylamino, aminoalkyleneamino, amino [poly(alkyleneamino)], bipyridyl and bipyridylamino and Y is as defined above; or, $R^1$ and $R^2$ taken together represent $-X-Y-X-$ wherein X and Y are as defined above.

2. A compound according to claim 1 wherein each q represents 1.

3. A compound according to claim 1 or claim 2 wherein $R^3$ and $R^4$ each represent methyl.

4. A compound according to any one of the preceding claims wherein both $R^1$ and $R^2$ are organic cations.

5. A compound according to claim 4 wherein $R^1$ and $R^2$ are selected from pyridinium, bipyridinium, alkylammonium, poly(alkylammonium), arylammonium and poly(arylammonium).

6. A compound according to claim 4 wherein $R^1$ and $R^2$ are selected from 2,2'-bipyridinium, 4,4'-bipyridinium and $[^+N(R^5)_2-R^6]_p-R^7$ wherein each $R^5$ independently is hydrogen or an alkyl group of from 1 to 4 carbon atoms; $R^6$ is an alkylene group of from 1 to 3 carbon atoms; $R^7$ is hydrogen or $-N(R^5)_3$ and p is an integer from 1 to 4.

7. A compound according to claim 6 wherein X is 4,4'-bipyridinium or $-[^+N(R^5)_2-R^6]_p-N^+(R^5)_2-$ wherein each $R^5$ independently is hydrogen or an alkyl group of from 1 to 4 carbon atoms; $R^6$ is an alkylene group of from 1 to 3 carbon atoms; $R^7$ is hydrogen or $-N(R^5)_3$ and p is an integer from 1 to 4.

8. A compound according to claim 1 wherein the cation is N,N'-bis (N,N',5'-trimethyl-2,2'-bipyridyl- 5-methylene)-N N,N', N'-tetramethyl-ethylene-diammonium; N,N'-dimethyl-5,5'-bis (N'-dimethyl-4,4'-bipyridinium-N-methylene)- 2,2'-bipyridyl; or, N,N'-bis(N,N',5'-trimethyl-2,2'-bipyridinium-5-methylene)-4,4'-bipyridinium.

* * * * *